(12) United States Patent
Engman

(10) Patent No.: US 10,238,497 B2
(45) Date of Patent: Mar. 26, 2019

(54) SURGICAL MEMBRANE

(71) Applicant: Neoss Limited, Yorkshire (GB)

(72) Inventor: Fredrik Nils Engman, Molnlycke (SE)

(73) Assignee: Neoss Limited, Harrogate (GB)

( * ) Notice: Subject to any disclaimer, the term of this patent is extended or adjusted under 35 U.S.C. 154(b) by 0 days.

(21) Appl. No.: 15/504,267

(22) PCT Filed: Sep. 30, 2015

(86) PCT No.: PCT/GB2015/052844
§ 371 (c)(1),
(2) Date: Feb. 15, 2017

(87) PCT Pub. No.: WO2016/051165
PCT Pub. Date: Apr. 7, 2016

(65) Prior Publication Data
US 2017/0239051 A1    Aug. 24, 2017

(30) Foreign Application Priority Data
Sep. 30, 2014 (GB) .................... 1417243.1

(51) Int. Cl.
*A61F 2/28* (2006.01)
*A61F 2/30* (2006.01)

(52) U.S. Cl.
CPC .......... *A61F 2/2846* (2013.01); *A61F 2/2803* (2013.01); *A61F 2002/30034* (2013.01); *A61F 2002/3068* (2013.01); *A61F 2002/30971* (2013.01); *A61F 2310/00023* (2013.01)

(58) Field of Classification Search
CPC .... A61F 2/2803; A61F 2/2846; A61F 2/2875; A61F 2002/3068; A61F 2002/30971; A61F 2002/2835; A61F 2013/00357; A61B 17/8085
See application file for complete search history.

(56) References Cited

U.S. PATENT DOCUMENTS

| | | | |
|---|---|---|---|
| 4,598,011 | A | 7/1986 | Bowman |
| 5,032,445 | A | 7/1991 | Scantlebury et al. |
| 5,093,179 | A | 3/1992 | Scantlebury et al. |
| 5,380,328 | A | 1/1995 | Morgan |
| 8,556,990 | B2 | 10/2013 | Bartee et al. |
| 2006/0224242 | A1 | 10/2006 | Swords et al. |
| 2008/0044449 | A1 | 2/2008 | McKay |
| 2013/0288199 | A1 | 10/2013 | Wen |

FOREIGN PATENT DOCUMENTS

| | | |
|---|---|---|
| DE | 4414675 C1 | 9/1995 |
| WO | WO2011/125760 A1 | 10/2011 |

*Primary Examiner* — Brian Dukert
(74) *Attorney, Agent, or Firm* — Shay Glenn LLP

(57) ABSTRACT

A reinforced surgical membrane for supporting bone growth by shielding a bone cavity from soft tissue in-growth comprises are a reinforcing layer (2) between a first membrane layer and a second membrane layer (4). The reinforcing layer (2) has defined therein an array of holes (3) which may connect the first and second membrane layers.

15 Claims, 6 Drawing Sheets

SURGICAL MEMBRANE

This invention relates to a reinforced membrane for use in surgery, particularly dental surgery.

BACKGROUND

It is known, for example from U.S. Pat. No. 4,598,011, U.S. Pat. No. 5,032,445, U.S. Pat. No. 5,093,179 and U.S. Pat. No. 8,556,990 to provide a reinforced PTFE membrane to assist in the growth of bone and tissue after trauma and surgery. The membrane acts as a barrier to prevent rapidly migrating connective tissue cells from entering a bone defect so that slower migrating cells with osteogenic potential can preferentially enter the bone defect and assist with bone growth.

For example, U.S. Pat. No. 8,556,990 discloses a reinforced PTFE membrane. According to that disclosure a portion of a bone defect is covered with a multilayered membrane that includes a reinforcing layer. A member of the reinforcing member is fastened to an area of bone and soft tissue is secured about the membrane. The membrane facilitates healing of the defect and/or otherwise improves a bone surface. One membrane comprises a plurality of layers that includes a binding layer and a PTFE layer which has a textured surface and a substantially smooth surface. The textured surface provides a top surface of the membrane and the substantially smooth surface contacts bone. According to U.S. Pat. No. 8,556,990, the reinforcing member is a titanium member provided with "fingers" which provide the necessary reinforcement.

The present invention, at least in its preferred embodiments seeks to provide an alternative construction of a reinforced surgical membrane.

BRIEF SUMMARY OF THE DISCLOSURE

In accordance with the present invention there is provided a reinforced surgical membrane for supporting bone growth by shielding a bone cavity from soft tissue ingrowth.

The membrane comprises a reinforcing layer between a first membrane layer and a second membrane layer. The reinforcing layer has defined therein an array of holes which may connect the first and second membrane layers. The first and second layers are connected at the periphery of the reinforcing layer and, preferably, the holes add to the connection of the two layers.

Thus in accordance with the invention, the reinforcing layer is provided with an array of holes. The array of holes may also be described as fenestrations. The array of holes allows continuous reinforcement of the membrane layers with retention of the membrane layers to the reinforcing layer which can avoid movement and thereby transgingival exposure of the reinforcing layer. The total reinforced area provided by the reinforcing layer can be substantially higher than prior art designs which provides better strength and stability during bone regeneration, but the total open membrane area for gas and liquid transportation may be increased due to the holes. The resultant membrane is easy to form in three dimensions because the reinforcing layer provides a continuous mesh. In one embodiment of the invention, there is higher retention between the two membrane layers due to the increased area between the two membrane layers through the array of holes providing easier and more secure shaping of the membrane and avoiding delamination.

Typically, more than 30% of the area defined by the perimeter of the reinforcing layer is occupied by the holes of the array. In embodiments of the invention more than 40%, 50%, 60%, 70% or even 80% of the area defined by the perimeter of the reinforcing layer is occupied by the holes of the array.

The array may comprise more than 10 holes. In embodiments of the invention the array may comprise more than 15 holes.

Typically, the holes are circular. However, this is not essential and other shapes are possible. The holes may have a diameter (width) of more than 0.1 mm, for example more than 0.5 mm. The holes may have a diameter (width) of less than 2 mm, for example less than 1.5 mm.

The array may be a regular array. For example, the holes may be arranged in rows and columns. However, the holes may be distributed in any suitable distribution.

The array may comprise at least one blind hole capable of containing a pharmaceutically active substance. Such a blind hole may act as a drug release compartment. A plurality of such blind holes may be provided.

The holes may be formed in the reinforcing layer by etching, stamping, water cutting or laser cutting, for example. Typically the reinforcing layer may be formed of titanium but different titanium alloys or medical grade stainless steels or PEEK materials can be used. The reinforcing layer may have a thickness of more than 0.1 mm. The reinforcing layer may have a thickness of less than 0.5 mm. The surface of the reinforcing layer can be adapted to increase adhesion to the membrane layers. The reinforcing layer is preferably made from a sheet or a foil material which is initially substantially flat, although the reinforcing layer may be curved or formed either in the delivered product or customizable (e.g. by being curved or formed) by the user.

In embodiments of the invention, the first and/or the second membrane layer comprises PTFE. In embodiments of the invention, the first and/or the second membrane layer or portions thereof comprises a resorbable material, such as for example collagens, polymers, sugar. The first membrane layer may have a different density to the second membrane layer. Typically the density of the first or second membrane layer is more than 1 g/cc. Typically the density of the first or second membrane layer is less than 5 g/cc. Thickness and surface characteristics such as roughness and morphology and/or the porosity may be different for each of the first and second membrane layers.

By having first and second membrane layers of different densities (and/or possibly different thicknesses and/or surface characteristics and/or porosity), it is possible to achieve specific healing responses for the different tissues such as soft and hard tissues, or to address different issues such as bacterial growth or to achieve expected bone growth. For example, one of the first and second membrane layers may comprise a relatively dense PTFE layer (e.g. monodirectional PTFE) with a tight texture that is designed to resist bacteria permeability and is suited to soft tissue. The other of the first and second membrane layers may comprise less dense and/or rough expanded PTFE (e.g. multidirectional PTFE) that is more suited to hard tissue integration. This combination results in a membrane that is easy to handle and protects the augmentation site in a predictable manner.

The first membrane layer may be bonded to the second membrane layer through the holes of the array.

In an embodiment, the first and/or second membrane layer is sufficiently non-porous or cell occlusive to prevent passage of bacteria and/or migration of soft tissue cells therethrough. This avoids contamination during bone formation or excessive adhesion of the hard and/or soft tissue to the membrane which would make the membrane more difficult to remove after use.

The membrane would typically be delivered as flat pieces but to facilitate the clinical usage adaptation to the clinical needs could be achieved by providing a membrane having a preformed non-planar configuration, for example a configuration including curved, dented or otherwise non-planar features.

BRIEF DESCRIPTION OF THE DRAWINGS

Embodiments of the invention are further described hereinafter with reference to the accompanying drawings, in which.

DETAILED DESCRIPTION

Figure 1:
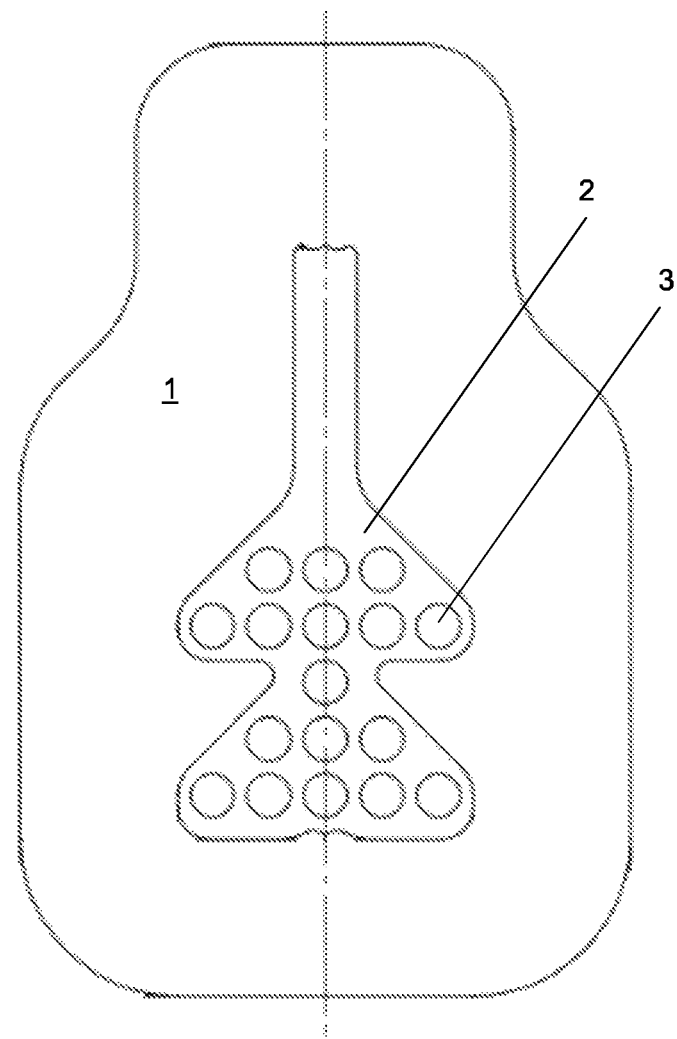
FIG. 1 shows a reinforced surgical membrane according to a first embodiment of the invention.

FIG. 1 shows a reinforced surgical membrane according to a first embodiment of the invention. The membrane comprises a first membrane layer 1 in the form of a PTFE membrane material. A titanium reinforcing layer 2 is provided on the first membrane layer 1. The reinforcing layer 2 is shaped with an outline according to the intended surgical location in which the surgical membrane is to be applied. Within the outline, the reinforcing layer 2 is provided with fenestrations in the form of an array (or "mesh") of holes 3 through the reinforcing layer 2. The reinforcing layer 2 may be enclosed by a further membrane layer 4 (not shown in FIG. 1 for clarity) which overlies the first membrane layer 1 and may have a corresponding outline as layer 1. The holes 3 in the reinforcing layer 2 allow the further membrane layer 4 to contact the first membrane layer 1 so that the two membrane layers 1, 4 may be mutually and/or additionally bonded to prevent delamination as the surgical membrane is shaped in use. The bonding of the membrane layers 1, 4 through the holes 3 allows for continuous reinforcement of the membrane by retaining the membrane layers to the reinforcing layer 2 even when the surgical membrane is shaped in use. The configuration of the reinforcing layer 2 shown in FIG. 1 has the advantage over "finger" arrangements known from the prior art that it can be more easily shaped in three dimensions as the mesh provides reinforcement across a continuous area of the surgical membrane, which provides better strength and stability during bone regeneration. Moreover, the holes 3 in the reinforcement layer allow gas and liquid transport through the membrane layers 1, 4.

Figure 2:
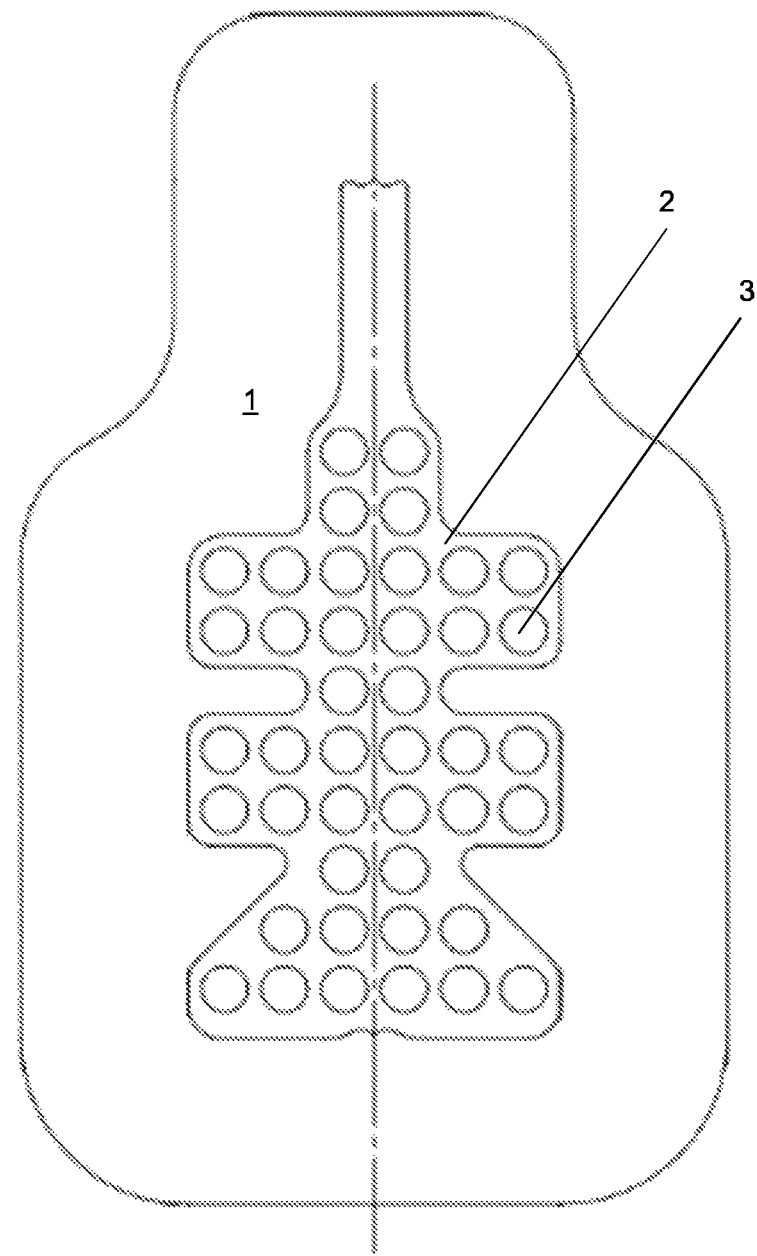
FIG. 2 shows a reinforced surgical membrane according to a second embodiment of the invention.
Figure 3:
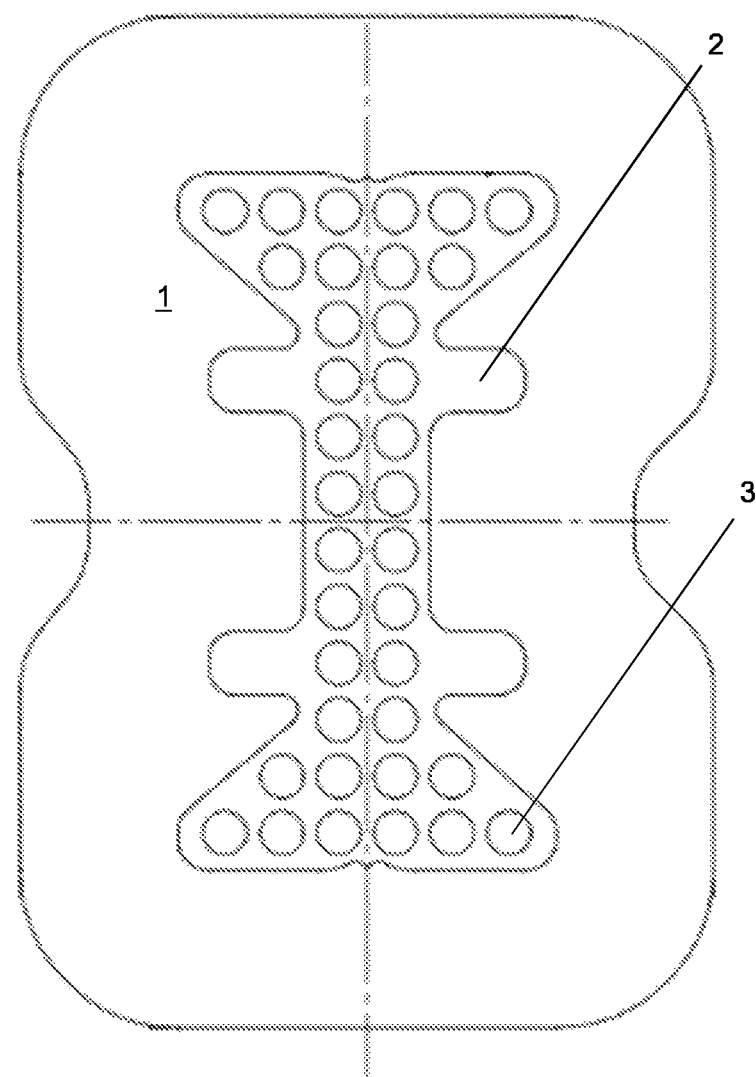
FIG. 3 shows a reinforced surgical membrane according to a third embodiment of the invention.
Figure 4:
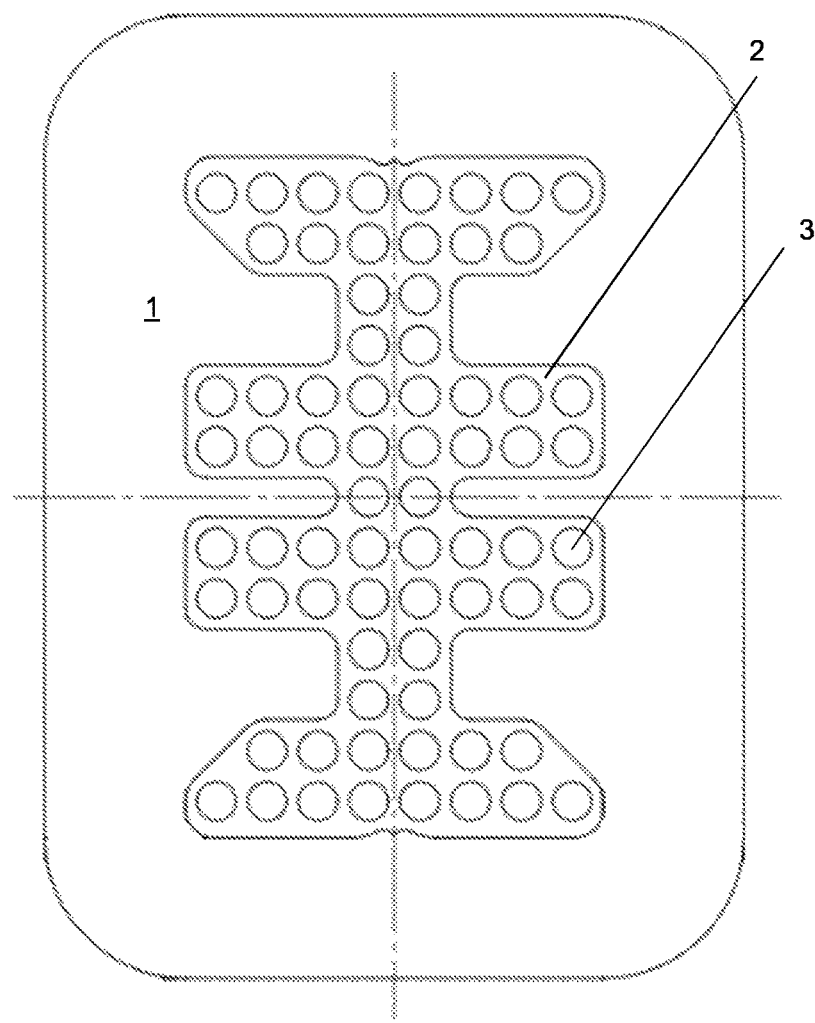
FIG. 4 shows a reinforced surgical membrane according to a fourth embodiment of the invention.

FIGS. 2 to 4 show reinforced surgical membranes according to second, third and fourth embodiments of the invention respectively, each for alternative clinical applications. The same reference numerals are used in all the Figures to represent corresponding features.

Figure 5:
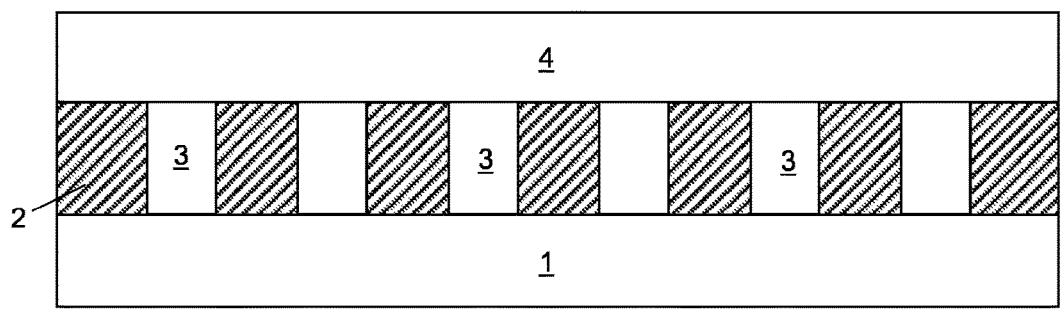
FIG. 5 is a schematic representation of a cross section through a reinforced surgical membrane according to an embodiment of the invention illustrating one configuration of the reinforcement.
Figure 6:
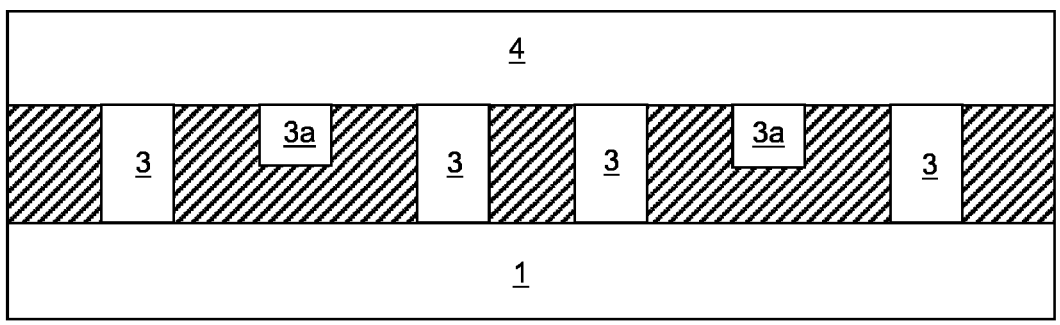
FIG. 6 is a schematic representation of a cross section through a reinforced surgical membrane according to an embodiment of the invention illustrating an alternative configuration of the reinforcement.

FIG. 5 is a schematic representation of a cross section through a reinforced surgical membrane according to an embodiment of the invention. As shown in FIG. 5, all of the holes 3 defined in the reinforcing layer 2 pass through the reinforcing layer 2 allowing the first membrane layer 1 and the further membrane layer 4 to connect. FIG. 6 shows an alternative configuration in a schematic cross-sectional view corresponding to FIG. 5. According to the alternative configuration, some of the holes in the array (or "mesh") are blind holes 3a. The blind holes 3a can be used as receptacles for pharmaceutically active substances. In this configuration, the further membrane layer 4 may be selected to allow controlled release of the pharmaceutically active substances. For example the further membrane layer 4 may be formed completely or partially of a resorbable material.

Figure 7:
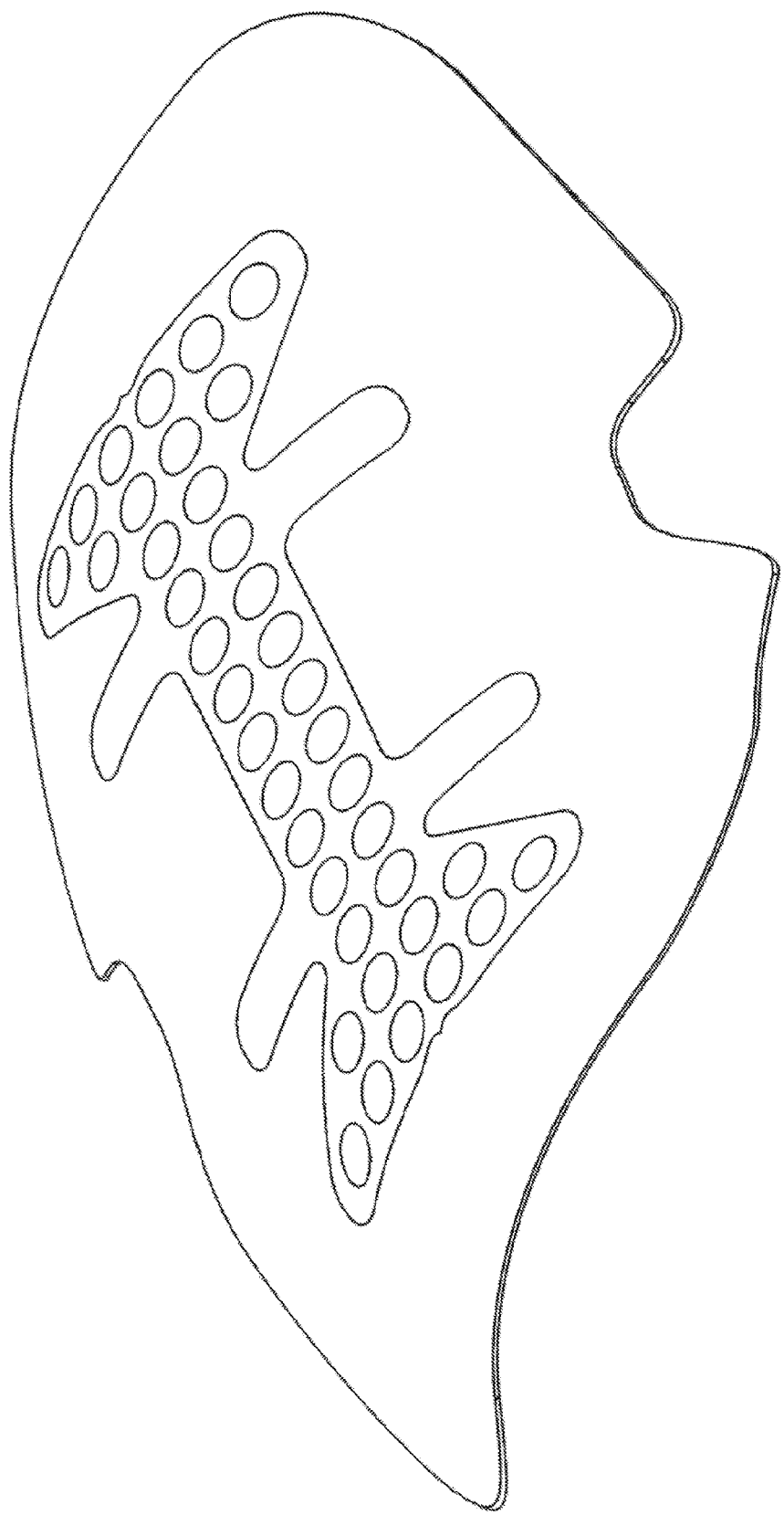
FIG. 7 is a schematic representation of a cross section through a reinforced surgical membrane according to an embodiment of the invention having a curved configuration compared to an embodiment having a flat configuration.

FIG. 7 shows a pre formed membrane X versus a flat membrane Y. The pre forming is made before delivery by for example using a press die. Different configurations representing different anatomical considerations can be offered to facilitate the handling and the function of the reinforced membrane.

In the illustrated embodiments, the titanium reinforcing layer 2 has a nominal thickness of 0.15 mm. The reinforcing layer 2 and the holes 3 therein may be formed by any suitable method, for example etching, stamping, water cutting or laser cutting.

The density and/or thickness of the membrane layers can be selected to address a wide range of different biological needs. For example, the first and second membrane layers 1, 4 may be made from the same material, having the same thickness, but having different densities, for example one layer of dense PTFE and another of expanded PTFE. In another embodiment, the starting materials of the first and second membrane layers might be identical (same material, same thickness, same density) but one of the layers might be compressed to give a denser layer, in use. In another embodiment, the first and second membrane layers might comprise different materials having different densities and/or different thicknesses. The overall density of the membrane may also be varied by selecting the thickness and/or density of the reinforcing layer 2.

In summary, a reinforced surgical membrane for supporting bone growth by shielding a bone cavity from soft tissue ingrowth comprises a reinforcing layer 2 between a first membrane layer 1 and a second membrane layer 4. The reinforcing layer 2 has defined therein an array of holes 3 which connect the first and second membrane layers. The membrane provides more continuous reinforcement with more retention of the membrane layers to the reinforcing mesh than designs of the prior art. This avoids movement and thereby transgingival exposure of the reinforcing mesh. The continuous reinforcing mesh makes the membrane easier to form in three dimensions. Retention between the two membrane layers is significantly increased due to increased area between the two membrane layers through the mesh holes providing easier and more secure shaping of the reinforcing mesh and avoiding delamination. The total reinforced areas is substantially higher than prior art designs providing better strength and stability during bone regeneration, while at the same time the total open membrane area for gas and liquid transportation may be increased due to the mesh holes. The production method is efficient, flexible, tooling cost minimal, allowing for any geometry and size for different materials to be made, including drug release chambers. The selection of properties of the membrane layers (density, surface, porosity, thickness, etc) can be adapted to address a much wider range of different biological needs as compared to existing membranes, hence enhancing the bone growth treatment.

Throughout the description and claims of this specification, the words "comprise" and "contain" and variations of them mean "including but not limited to", and they are not intended to (and do not) exclude other additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A reinforced surgical membrane for supporting bone growth by shielding a bone cavity from soft tissue ingrowth, the membrane comprising a reinforcing layer between a first membrane layer and a second membrane layer, wherein the reinforcing layer has defined therein an array of holes and wherein a material of the first membrane layer has a different density and/or thickness to a material of the second membrane layer prior to implantation.

2. A membrane as claimed in claim 1 wherein the holes connect the first and second membrane layers.

3. A membrane as claimed in claim 1, wherein the reinforcing layer has a perimeter, and wherein more than 50% of an area defined by the perimeter is occupied by the holes of the array.

4. A membrane is claimed in claim 1, wherein the array comprises more than 10 holes.

5. A membrane as claimed in claim 1, wherein the array is a regular array.

6. A reinforced surgical membrane for supporting bone growth by shielding a bone cavity from soft tissue ingrowth, the membrane comprising a reinforcing layer between a first membrane layer and a second membrane layer, wherein the reinforcing layer has defined therein an array of holes and wherein the first membrane layer has a different density and/or thickness to the second membrane layer, wherein the array comprises at least one blind hole capable of containing a pharmaceutically active substance.

7. A membrane as claimed in claim 1, wherein the holes are formed in the reinforcing layer by etching, stamping, water cutting or laser cutting.

8. A membrane as claimed in claim 1, wherein the first and/or the second membrane layer, or portions thereof, comprises PTFE.

9. A membrane as claimed in claim 1, wherein the first and/or the second membrane layer, or portions thereof, comprise a resorbable material.

10. A membrane as claimed in claim 1, wherein the first and/or the second membrane layer, or portions thereof, comprise multidirectional PTFE, monodirectional PTFE or a combination thereof.

11. A membrane as claimed in claim 1, wherein the reinforcing layer comprises titanium, titanium alloys, medical grade stainless steel or PEEK.

12. A membrane as claimed in claim 1, wherein a surface of the reinforcing layer is adapted to increase adhesion to one or both of the membrane layers.

13. A membrane as claimed in claim 1, wherein the membrane has a preformed non-planar configuration.

14. A membrane as claimed in claim 1, wherein the first and/or second membrane layer is sufficiently non-porous to prevent passage of bacteria and/or migration of soft tissue cells therethrough.

15. A reinforced surgical membrane for supporting bone growth by shielding a bone cavity from soft tissue ingrowth, the membrane comprising a reinforcing layer between a first membrane layer and a second membrane layer, the first membrane layer comprising a first material and the second membrane layer comprising a second material that is different to the first material, wherein the reinforcing layer has defined therein an array of holes and wherein the first material of the first membrane layer has a different density and/or thickness to the second material of the second membrane layer.

* * * * *